United States Patent [19]

Horikoshi

[11] Patent Number: 5,190,874
[45] Date of Patent: Mar. 2, 1993

[54] METHOD FOR PRODUCING PENICILLINASE AND XYLANASE

[75] Inventor: Koki Horikoshi, Tokyo, Japan
[73] Assignee: Rikagaku Kenkyusho, Wako, Japan
[21] Appl. No.: 401,507
[22] Filed: Aug. 30, 1989

Related U.S. Application Data

[63] Continuation of Ser. No. 265,281, Oct. 25, 1988, abandoned, which is a continuation of Ser. No. 814,793, Dec. 30, 1985, abandoned.

[30] Foreign Application Priority Data

Dec. 28, 1984 [JP] Japan .................. 59-278681

[51] Int. Cl.$^5$ .................. C12N 9/24; C12N 1/21; C12N 15/70
[52] U.S. Cl. .................. 435/200; 435/252.33; 435/320.1
[58] Field of Search .................. 435/68, 170, 172.1, 435/172.3, 253, 91, 320, 822, 832, 849, 69.1, 71.1, 200, 252.3, 252.33; 536/27; 935/6, 9, 11, 14, 22, 23, 26, 27, 24, 50, 60, 66, 72, 73

[56] References Cited

U.S. PATENT DOCUMENTS 4,411,994 10/1983 Gilbert et al. .................. 435/71
4,624,922 11/1986 Horikoshi et al. .................. 435/172.3

FOREIGN PATENT DOCUMENTS 0121138 10/1984 European Pat. Off.

OTHER PUBLICATIONS

Chang, C., et al., Gene, 44, 121–125 (1986).
Bell, G., et al., Nature, 282, 525–527 (1979).
Ikemara, M. et al., PNAS USA, 81, 5956–5960 (1984).
Ohno, S., et al., PNAS USA, 78, 5305–5309 (1981).
Kudo et al. 1983, *J. Bacteriol.* 156(2): 949–951.
Kudo et al. 1984, *J. Gen. Microbiol.* 131: 2825–2830.
Kudo et al. 1984, *J. Bacteriol.* 155: 601–605.
Bernier et al. 1983 Gene 26: 59–65.
Chakraborty et al. 1984, Infect. Immun. 46: 435–441.
FEMS Microbiology letters 36 (1986), 31–34, Kato, C. et al., "Construction . . . *Escherichia coli*".
Gene, 54 (1987) 197–202 Kato, C. et al., "Construction . . . *Escherichia coli*".
Agricultural and Biological Chemistry, vol. 50, No. 4, 1986, pp. 1067, 1068; C. Kato et al., "Extracellular Production of Xylanase".
Chemical Abstracts, vol. 86, No. 19, 9th May 1977, p. 264, abst. No. 136179y, Columbus, Ohio, US; R. L. Rodriguez et al.: "Construction and Characterization of Cloning Vehicles", & INC-UCLA Symp. Mol. Cell. Biol. 1976, 5 (Mol. Mech. Control Gene Expression), 471–7.
Chemical Abstracts, vol. 103, No. 25, 23rd Dec. 1985, p. 272, Abst. No. 208072c, Columbus, Ohio, US; T. Kudo et al.: "Molecular Cloning and Expression of a Xylanase Gene of Alkalophilic Aeromonas sp. No. 212 in *Escherichia coli*", & J. Gen. Microbiol. 1985, 131(10), 2825–30.
Chemical Abstracts, vol. 105, No. 9, 1st Sep. 1986, p. 154, Abstract No. 73432p, Columbus, Ohio, US; T. Kobayashi et al.: "Excretion of the Penicillinase of Alkalophilic Bacillus . . . in Plasmid pMB9", & J. Bacteriol. 1986, 166(3), 728–32.

*Primary Examiner*—Richard A. Schwartz
*Attorney, Agent, or Firm*—Oblon, Spivak, McClelland, Maier & Neustadt

[57] ABSTRACT

A novel plasmid pXP102-3 which is constructed from Aeromonas sp. No. 212 chromosomal DNA fragment coding for production of xylanase and a vector plasmid pEAP2 carrying a DNA fragment coding for production and secretion of penicillinase. A novel microorganism, *Escherichia coli* HB101 (pXP102-3), containing the plasmid pXP102-3 and being capable of producing and secreting penicillinase and xylanase. A method for cultivation of the microorganism characterized in that it is cultured in a broth containing NaCl for 12 to 48 hours.

12 Claims, 6 Drawing Sheets

METHOD FOR PRODUCING PENICILLINASE AND XYLANASE

This application is a continuation of application Ser. No. 07/265,281, filed on Oct. 25, 1988, now abandoned, which is a continuation of application Ser. No. 06/814,793, filed on Dec. 30, 1985, now abandoned.

BACKGROUND OF THE INVENTION (1) Field of the Invention

This invention relates to a novel plasmid, a method for construction of the plasmid, a novel microorganism containing the plasmid, and a method for cultivation of the microorganism and relates more particularly to a novel plasmid with DNA coding for production and extracellular secretion of such high-molecular substance as xylanase, penicillinase or beta-galactosidase, a novel microorganism transformed with the plasmid, and a method for production and secretion of such high-molecular substance by culturing the microorganism.

(2) Description of the Prior Art

A plasmid is a non-chromosomal gene of cyclic DNA found in a microorganism cell. Plasmids are currently being used as means for recombination of microorganism genes and are becoming more and more important in the fermentation industry.

Studies have recently been done on plasmids carrying foreign DNA having genetic information of metabolic products or specific demand for growth of microorganism, as shown in the production of amino acids or peptides. Some plasmids have been introduced into host microorganisms to obtain transformants. Methods have been proposed for producing relatively low molecular compounds such as amino acids and peptides by culturing the transformants. However, the degree of propagation of plasmids carrying genes for production of high-molecular substances depends on the nature of the host microorganisms and these plasmids have not effectively been expressed. Furthermore, no effective methods for cultivation of such transformants have been established.

It has not been possible to obtain a certain extracellular high-molecular product by culturing a microorganism transformed with a plasmid carrying a foreign DNA fragment having genetic information of extracellular secretion of high-molecular substances which are metabolic products of another microorganism. However, such extracellular secretion has not been successful even using a transformant of Escherichia species, which is the most commonly used host microorganism.

U.S. Pat. No. 4,411,994 of W. Gilbert et al discloses a process for producing specific proteins in bacteria and having them excreted from the bacterial cell. This process comprises inserting the DNA representing the desired non-bacterial protein or part of a protein by recombinant techniques into a plasmid or phage gene for either a periplasmic or an extracellular protein, hereinafter called a "carrier protein", transforming a bacterial host with the recombinant gene, and culturing the transformed host to excrete the protein. The process of this patent provides a means for producing a selected protein by employing a gene for a carrier protein which has a leader sequence of hydrophobic amino acids at its amino terminus.

The cell wall of *Escherichia coli*, which has often been used for production of useful physiologically active substances, consists of three kinds of membrane: inner membrane, peptide glycan and outer membrane. The space between the inner and outer membrane is called the periplasmic space. The process of U.S. Pat. No. 4,411,994 has succeeded in the excretion of the products within the periplasmic space but not within the culture medium through the outer membrane or outside the bacterial host cell.

The inventors of this invention previously constructed a plasmid carrying a DNA fragment prepared from chromosomal DNA of a Bacillus strain, and coding for production and extracellular secretion of penicillinase. They introduced the plasmid into *Escherichia coli* HB101 to obtain a transformant, *Escherichia coli* HB101 (pEAP2), capable of producing and secreting penicillinase (Japanese Patent Unexamined Publication No. 59-162886).

Further, they succeeded in the construction of a plasmid carrying a DNA fragment prepared from chromosomal DNA of a Bacillus strain and coding for production and extracellular secretion of xylanase. They introduced the plasmid into *Escherichia coli* HB101 to obtain a transformant, *Escherichia coli* HB101 (pCX311), having an ability to produce and secrete xylanase (Japanese Patent Application No. 58-232508).

By culturing such a strain containing a plasmid carrying a DNA fragment coding for production and secretion of useful physiologically active substances such as enzymes, it is possible to separate and collect the active substances directly from the culture medium in a greater amount and in a more purified form because there is no need for crushing the cells of the strain and there is no saturation of the active substances within the cells.

However, useful physiollogically active substances are ordinarily accumulated mainly within cells and up to now there have been known only restricted numbers of microorganisms which produce and secrete the useful physiologically active substance into media. Therefore, it is very useful from the industrial point of view to establish a method in which it is possible to create a desired strain which produces and secretes a desired useful physiologically active substance into media.

SUMMARY OF THE INVENTION

Therefore, an object of this invention is to provide a novel plasmid which gives a microorganism transformed therewith the ability to produce and secrete a useful physiologically active substance.

Another object of this invention is to provide a method for construction of such plasmid, a novel microorganism transformed with the same and a method for culturing the microorganism to obtain a useful physiologically active substance.

This invention provides a plasmid which provides a host with the ability to produce and secrete a useful physiologically active substance and which is constructed by inserting a DNA fragment coding for production of said active substance into a vector plasmid containing a DNA fragment coding for production and secretion of penicillinase. More specifically the plasmid can be constructed by a process which comprises preparing, with a restriction enzyme, the chromosomal DNA fragment coding for production of the active substance, cleaving the vector plasmid containing the DNA fragment coding for production and secretion of penicillinase with a restriction enzyme, treating the chromosomal DNA fragment and the cleaved vector plasmid with a ligase to form a recombinant plasmid and isolating the same.

This invention provides a novel microorganism which is prepared by transforming a strain of the genus Escherichia with the plasmid of this invention and which produces and secretes the active substance into media.

This invention further provides a method for cultivation of the microorganism to obtain the active substance produced inside the bacterial cell and secreted outside it, which comprises inoculating the microorganism in a culture medium containing a selected carbon source together with an inorganic salt necessary for the microorganism to grow, and continuing to culture the microorganism after the concentration of the microorganism cells reaches the maximum and until the production and accumulation of the active substances in the medium reach the maximum.

DETAILED DESCRIPTION OF THE INVENTION

The term "useful physiologically active substance" used in the specification and the claims of this application means a high-molecular weight physiologically active compound such as an enzyme, e.g., penicillinase, xylanase, betagalactosidase, beta-lactamase or alkaline phosphatase, or insulin, human growth hormone, interferon, antibiotic, etc.

According to the preferred embodiment of this invention, there is provided a plasmid which provides a host with an ability to produce and secrete both penicillinase and xylanase. The plasmid is constructed by inserting a DNA fragment coding for production and secretion of penicillinase (hereinafter referred to as "penicillinase DNA fragment") and a DNA fragment coding for production of xylanase (hereinafter referred to as "xylanase DNA fragment") into a vector plasmid.

The plasmid of this invention can be constructed by inserting the xylanase DNA fragment at the cleavage site of a plasmid vector having the penicillinase DNA fragment inserted thereinto.

Vector DNA

A vector DNA which can be used in this invention is one constructed by inserting the penicillinase DNA fragment at cleavage sites of a plasmid such as Col $E_1$, pMB9, pSC101, R6K, lambda phage and a typical example is the pEAP2 plasmid which is constructed by inserting the penicillinase DNA fragment prepared from a strain of the genus Bacillus into pMB9 plasmid. The pEAP2 plasmid can be constructed, for example, as follows.

Alkalophilic Bacillus No. 170 (FERM BP-467) having the ability to produce and secrete penicillinase is cultured with shaking at 30° C. for 19 hours in a broth containing 2.0 g of glycerol, 5.0 g of yeast extract, 5.0 g of polypeptone, 1.0 g of $K_2HPO_4$, 0.2 g of $MgSO_4\cdot 7H_2O$ and 10 g of $NaHCO_3$ in one liter of water and adjusted to pH 6.0. The cells in the latter logarithmic phase are collected, and a chromosomal DNA is extracted therefrom by the phenol extraction method and purified.

The chromosomal DNA is digested with the restriction enzyme Hind III at 37° C. for 5, 10, 20, 30 and 60 minutes to obtain DNA fragments.

Plasmid pMB9 (Bethesda Research Laboratories, U.S.A., tetracyclin resistant (Tetr)) used as a vector is cut with Hind III, then heated at 65° C. for 5 minutes, and then mixed with the DNA fragments. The mixture is treated with $T_4$ phage DNA ligase and then heated at 65° C. for 5 minutes.

Three-fold volume of ethanol is added to the mixture. Plasmids carrying the chromosomal DNA fragments are precipitated and collected.

The plasmids thus obtained are introduced into a host. The transformant having desired characteristics is selected and propagated to clone the pEAP2 plasmid. As such a host, a microorganism of the genus Escherichia can be suitably used and one typical example is *Escherichia coli* HB101 which is a hybrid strain of *Escherichia coli* K-12 and *Escherichia coli* (Molecular Cloning, A Laboratory Manual, p.504 (1982), Genotype: F−, hsd S 20($r_B$−, $m_B$−), rec A13, ara-14, proA2, lacY1, galK2, rpsL20(Sm'), xyl-5, mtl-1, supE44[31]).

Transformation with the pEAP2 plasmid will now be illustrated.

*Escherichia coli* HB101 is inoculated in 10 ml of LB-broth (containing 10 g of tryptone (Difco Laboratories, Detroit, Mich.), 5 g of yeast extract, 1 g of glucose and 10 g of NaCl in one liter of deionized water; pH is adjusted to 7.0) and culturing is carried out at 37° C. with shaking until the latter logarithmic phase. The cells are collected and suspended in an ice-cooled 0.03M $CaCl_2$ solution of (final concentration) to obtain competent cells. The cell suspension and the plasmid solution are combined and kept on ice for 60 minutes. The mixture is heated to 42° C. for 1 to 2 minutes to introduce the plasmid DNA into the cells. This cell suspension is inoculated in fresh LB-broth and cultured at 37° C. for 3 to 5 hours with shaking. The cells are collected and washed to obtain transformants, and *Escherichia coli* HB101 (pEAP2) (FERM BP-468) is isolated therefrom.

*Escherichia coli* HB101 (pEAP2) has the same microbiological properties as those of the host *Esherichia coli* HB101 except that it is penicillin resistant and has the ability to produce and secrete penicillinase. The transformant *Escherichia coli* HB101 (pEAP2) is propagated. The cells are collected and the pEAP2 plasmid are isolated.

The plasmid pEAP2 is a cyclic DNA molecule of about 7.7 kb containing the penicillinase DNA fragment of about 2.0 kb prepared from the chromosomal DNA of Bacillus No. 170, the fragment being inserted between the Hind III restricted site of the plasmid pMB9.

Figure 1:
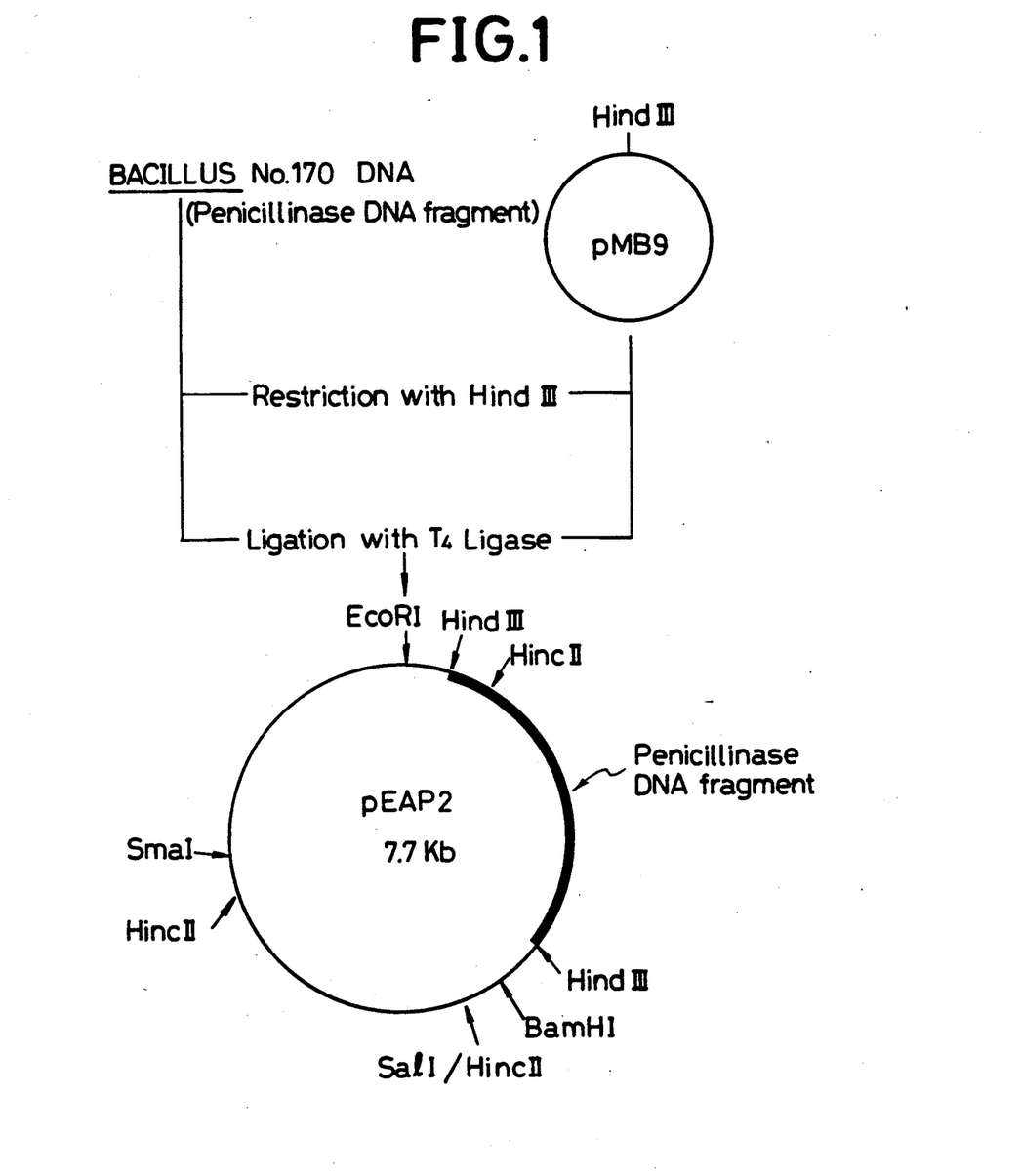
FIG. 1 shows a scheme for illustrating the process for construction of the plasmid, pEAP2, and the restriction enzyme cleavage map therefor.

A process for construction of the plasmid pEAP2 and the restriction enzyme cleavage map therefor are as shown in FIG. 1.

Preparation of the xylanase DNA fragment

One example of microorganisms containing the xylanase DNA fragment is a strain of the genus Aeromonas, one example of which is Aeromonas sp. No. 212 (ATCC 31085) The American Type Culture Collection Catalogue of Strains I 14th edition 1980; (Horikoshi K, Akiba T (1982) Alkalophilic Microorganisms, P 158 Springer, Berlin Heidelberg New York). Aeromonas sp. No. 212 (ATCC 31085) is cultured in a broth (containing 0.5% ammonium sulfate, 1.5% pulp flock, 0.02% glucose, 0.1% yeast extract, 0.02% $MgSO_4 \cdot 7H_2O$ and 0.2% $K_2HPO_4$ which has been adjusted to pH9 with 7% $NaHCO_3$ solution in water) with shaking at 37° C. for 10 hours. The cells in the latter logarithmic phase are collected, and chromosomal DNA is extracted therefrom by the phenol extraction method and purified.

Cloning of the chromosomal DNA is carried out as follows. The chromosomal DNA is cleaved with the restriction enzyme Hind III to obtain DNA fragments. A vector plasmid, pBR322 (Bethesda Research Laboratories, U.S.A., tetracyclin resistant ($Tc^r$) and ampicillin resistant ($Amp^r$)), is fully cleaved with Hind III, then heated at 65° C. for 5 minutes, and then mixed with the DNA fragments. The mixture is treated with $T_4$ phage DNA ligase to insert the fragments between the Hind III restricted site of the plasmid pBR322. Ethanol is added to the mixture. Plasmids carrying the chromosomal DNA fragments are precipitated and collected.

Escherichia coli HB101 is inoculated in 10 ml of LB broth (not containing glucose but containing 10 g of tryptone (Difco Laboratories, Detroit, Mich.), 5 g of yeast extract, 20 gamma of ampicillin and 10 g of NaCl in one liter of deionized water and adjusted to pH 7.0) and cultured at 37° C. with shaking until the latter logarithmic phase. The cells are collected and suspended under ice-cooled condition in 0.03M $CaCl_2$ solution (final concentration) in water to obtain competent cells. The cell suspension and the plasmid solution are combined and kept under ice-cooled condition for 60 minutes. The mixture is heated at 42° C. for 1 to 2 minutes to introduce the plasmid DNA into the cells. This cell suspension is inoculated in a broth containing 100 gamma of ampicillin and 0.5% of xylan and cultured. A strain having ampicillin resistance and xylanase activity is isolated.

The strain thus obtained contains the plasmid pAX1in which the chromosomal DNA fragment has been inserted and it has the ability to produce xylanase but not to secrete it. The strain is propagated and the cells are collected, whereafter the plasmid pAX1is isolated therefrom. The plasmid pAX1is cleaved with Hind III to obtain a cloned xylanase DNA fragment.

The plasmid pAX1is a cyclic DNA molecule of about 10.4 kb containing the xylanase DNA fragment of about 6.0 kb prepared from the chromosomal DNA of Aeromonas sp. No. 212, the fragment being inserted between the Hind III restricted site of the plasmid pBR322.

Figure 2:
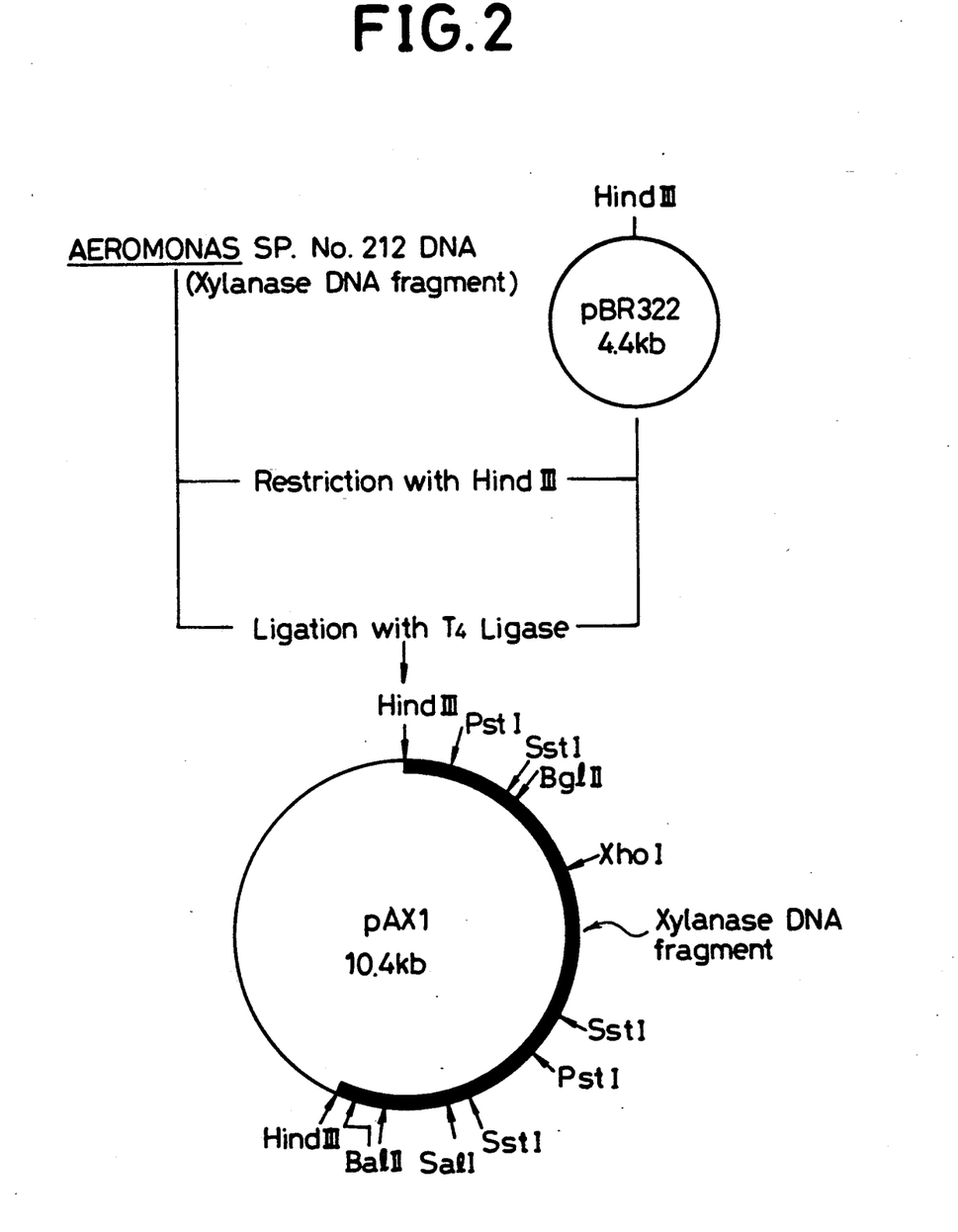
FIG. 2 shows a scheme for illustrating the process for construction of the plasmid, pAX1, and the restriction enzyme cleavage map therefor.

A process for construction of the plasmid pAX1and the restriction enzyme cleavage map therefor are as shown in FIG. 2.

Construction of the plasmid of this invention

The plasmid of this invention can,, be constructed for example, by a conventional method such as the so called shot gun method, for inserting a DNA fragment coding for production of useful physiologically active substance (e.g., the xylanase DNA fragment) into the vector DNA. Construction of the plasmid of this invention will now be explained by the following example in which the plasmid pEAP2 is used as a vector plasmid and the DNA fragment obtained by cleaving the plasmid pAX1containing the chromosomal DNA of Aeromonas sp. No. 212 with Bgl II as a xylanase DNA fragment.

The plasmid pAX1containing the xylanase DNA fragment is cleaved with the restriction enzyme BglII at 37° C. for 60 minutes to obtain the xylanase DNA fragments. The vector plasmid pEAP2 containing the penicillinase DNA fragment is fully cleaved with the restriction enzyme BamHI, then heated at 65° C. for 5 minutes, and then mixed with the xylanase DNA fragments. The mixture is treated with $T_4$ phage DNA ligase to insert the fragments between the Bam HI restricted site of the plasmid pEAP2 and then heated at 65° C. for 5 minutes.

Cleavage of the plasmid thus obtained with Bam HI and Bgl II is conducted again to concentrate the plasmid pXP102-3.

Escherichia coli HB101 is inoculated in 10 ml of LB broth (not containing glucose but containing 10 g of tryptone (Difco), 5 g of yeast extract, 20 µg/ml of ampicillin and 10 g of NaCl and adjusted to pH 7.0) and cultured at 37° C. with shaking until the latter logarithmic phase. The cells are collected and suspended under ice-cooled condition in 0.03M $CaCl_2$ solution (final concentration) in water to obtain competent cells. The cell suspension and the plasmid solution are combined and kept under ice-cooled condition for 60 minutes. The mixture is heated at 42° C. for 1 to 2 minutes to introduce the plasmid DNA into the cells. This cell suspension is inoculated in a broth containing 20 µg/ml of ampicillin and 0.5% of xylan and cultured. A strain having ampicillin resistance and xylanase activity is isolated.

The transformant Escherichia coli HB101 (pXP102-3) contains the plasmid pXP102-3 in which the chromosomal DNA has been inserted and it has the ability to produce and secrete both penicillinase and xylanase.

The strain Escherichia coli HB101 (pXP102-3) is propagated and the cells are collected, whereafter the plasmid pXP102-3 is isolated therefrom.

The plasmid pXP102-3 is a cyclic DNA molecule of 11.7 kb containing the xylanase DNA fragment prepared from the chromosomal DNA of Aeromonas sp. No. 212, the fragment being inserted between the BamHI restricted site of the plasmid pEAP2.

Figure 3:
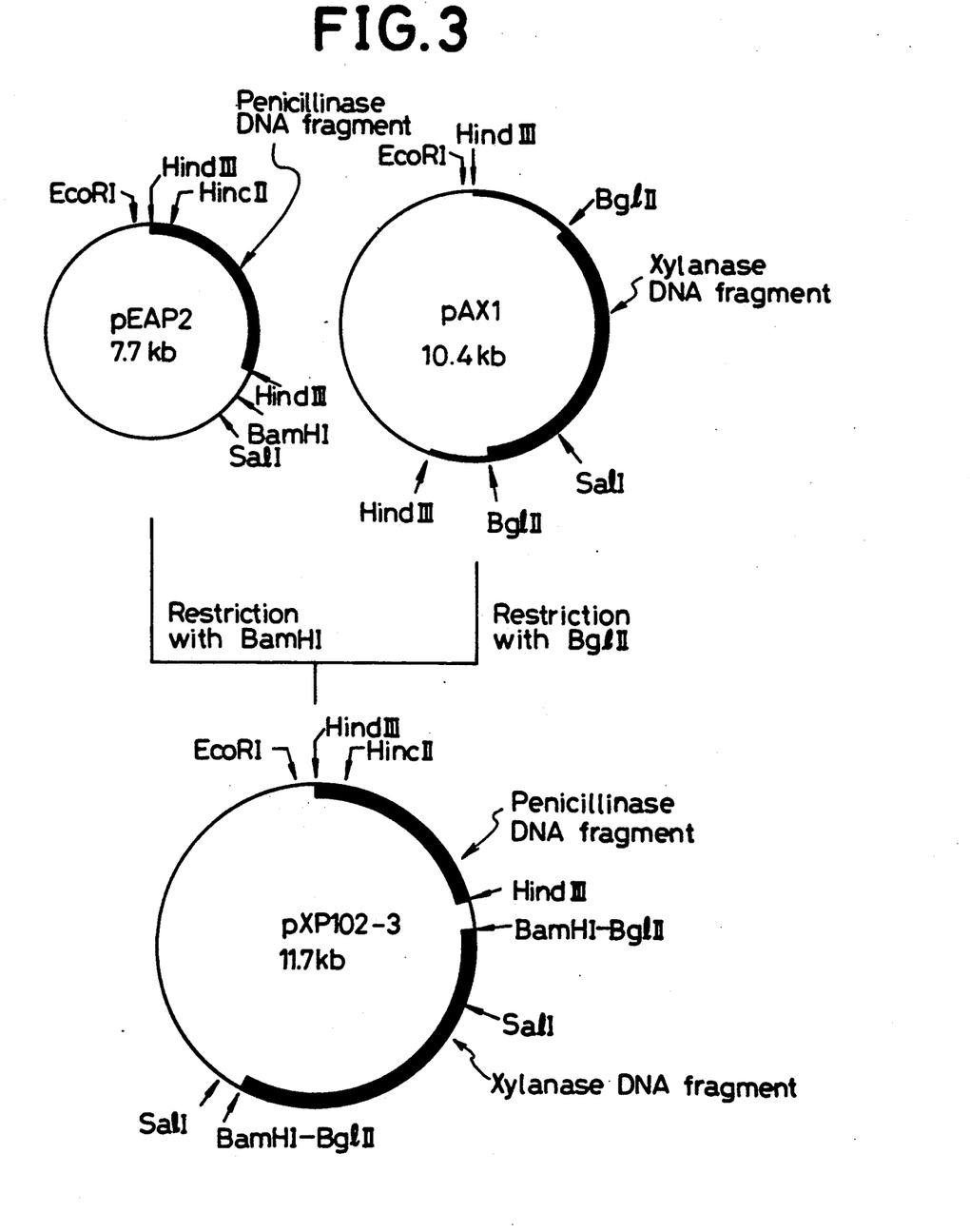
FIG. 3 shows a scheme for illustrating the process for construction of the plasmid, pXP102-3, and the restriction enzyme cleavage map therefor.

A process for construction of the plasmid pXP102-3 and the restriction enzyme cleavage map therefor are as shown in FIG. 3.

Escherichia coli HB101 (pXP102-3) has the same microbiological properties as those of the host, Escherichia coli HB101 except that it has penicillin resistance and the ability to produce and secrete both penicillinase and xylanase.

Thus, Escherichia coli HB101 (pXP102-3) can be cultured under the same cultivation conditions as the parent strain, Esherichia coli HB101, to produce and secrete both penicillinase and xylanase.

Cultivation of the microorganism

For culturing the transformant of this invention, there can be used any culture media suitable for the production of specific substances for which specific genetic information codes and suitable for growth of the microorganisms of the genus Escherichia. In the process of the present invention, it is possible to culture the microorganism in a culture medium containing an inorganic salt necessary for the microorganism to grow together with or without a carbon source, and to continue culturing the microorganism after the concentration of the microorganism cells reaches the maximum, and until the production and accumulation of the physiologically active substances in the media reach the maximum. It is preferred to use a medium not containing a carbon source as described below for accelerating the secretion of the physiologically active substance.

Examples of the inorganic salt which can be used in the present invention include sodium and potassium salts such as sodium chloride, sodium sulfate, potassium chloride and the like, among which sodium chloride is preferred. Examples of carbon sources include glucose, sucrose, lactose, maltose, glycerol, bran, xylan and the like. The media which can be used in this invention may contain such nitrogen sources as ammonia water, ammonium salts and the like, inorganic ions and optionally such nutrients as amino acids, vitamins and the like. Typical examples of the media which can be used in the present invention are those which use, as a basic medium, LB-broth (containing tryptone, yeast extract and NaCl), BPB-broth (Difco Laboratories; containing polypeptone, yeast extract and $K_2HPO_4$), nutrient broth (Difco 0001), tryptone-NaCl broth or the like.

Since almost all products remain in the intracellular fraction in a medium containing no inorganic salt, it is necessary to use a medium containing an inorganic salt so that most products will be secreted out of the cells into the culture medium. The amount of inorganic salt used is in the range of 0.1–3.0% by weight on the basis of the culture medium.

Although culture conditions such as pH, temperature, oxygen supply or the like can e changed for the optimum growth of the mircoorganism of the genus Escherichia, it is necessary in the present invention to continue culturing the microorganism after the concentration of the microorganism cells reaches the maximum, that is to say, after the latter logarithmic phase and until the production and accumulation of the high-molecular substances in the medium reach the maximum.

After the inoculation of the microorganism of the genus Escherichia in the medium, the cell concentration reaches the maximum in 5 to 20 hours and the production and accumulation of the high-molecular substances reach the maximum in 12 to 48 hours. Although the pH of the culture medium is not critical, it is preferred to be in the range of pH5–pH8, with a pH of 7 being especially preferred. Thus, without further addition of inorganic salt necessary for the microorganism to grow, carbon sources and the like during cultivation, the microorganism produces and secretes large amounts of physiologically active substances which can readily be collected.

According to the culture method of the present invention, in addition to enzyme proteins, such fermentation products as antibiotics, polysaccharides can be produced in a significant amount into media. This method can be applied to the cultivation of any microorganisms transformed with a plasmid carrying a foreign DNA coding for biologically active substances such as hormone peptide (e.g. insulin) or interferon and the DNA coding for production and secretion of biologically active substances, which enables mass production of biologically active substances such as insulin, interferon and the like.

As explained above, the present invention contributes to the industrial production of useful biologically active substances.

Examples of microorganisms which may be used in this invention include (i) Bacillus sp. No. 170, (ii) *Escherichia coli* HB101 (pEAP2), (iii) Aeromonas sp. No. 212, (iv) *Escherichia coli* HB101 (pAX1) and (v) *Escherichia coli* HB101 (pXP102-3). The microorganisms (i), (ii), (iv) and (v) were deposited with the Fermentation Research Institute, Agency of Industrial Science and Technology, Ministry of International Trade and Industry, Japan, International Depository Authority (hereinafter referred to as "FERM") under the following accession numbers, respectively, FERM BP-467, FERM BP-468, FERM BP-950 and FERM BP-951 (deposition dates May 1, 1981, Mar. 1, 1983, Jun. 1, 1984, and Jun. 1, 1984, respectively) and are on deposit with FERM in an unrestricted deposit permitting the full access to the culture, and the microorganism (iii) was deposited with the American Type Culture Collection under the accession number of ATCC 31085.

The depository and accession numbers of the above mentioned microorganisms are shown below:

| Microorganisms | Depository | Accession No. |
| --- | --- | --- |
| (i) Bacillus sp. No. 170 | FERM | FERM BP-467 |
| (ii) *Escherichia coli* HB101 (pEAP2) | FERM | FERM BP-468 |
| (iii) Aeromonas sp. No. 212 | ATCC | ATCC 31085 |
| (iv) *Escherichia coli* HB101 (pAX1) | FERM | FERM BP-950 |
| (v) *Escherichia coli* HB101 (pXP102-3) | FERM | FERM BP-951 |

The applicants will irrevocably remove all restrictions on the availability on the granting of a patent and will maintain the deposition of FERM BP-467, FERM BP-468, FERM BP-950 and FERM BP-951 in the unrestricted form until the end of the duration of a patent granted on this application if a patent is granted on this application, and thus said microorganism strains will be available to any third party at any time until the end of the duration of the patent granted on this application.

This invention provides a plasmid which can be constructed by inserting a chromosomal DNA fragment coding for production but not secretion of a useful physiologically active substance such as xylanase between a restriction enzyme cloven site of a vector plasid which provides a host with the ability to produce and secrete penicillinase. The plasmid thus constructed provides a host with the ability to produce and secrete the useful physiologically active substance (e.g., xylanase) in addition to penicillinase. It is therefore possible, according to this invention, to construct a new plasmid which provides a host such as *Escherichia coli* with the ability of production and secretion of useful physiologically active substances such as insulin, human growth hormone, interferon, enzyme, and the like and to create a useful microorganism having the ability to produce and secrete such useful substance.

We will now explain, with reference to Examples, methods for construction of the plasmids of the present invention, methods for preparation of the transformant, *Escherichia coli* HB101 (pXP102-3), and the production and secretion of penicillinase, xylanase and so on by the transformant.

EXAMPLE 1

Construction of the plasmid pEAP2

Alkalophilic Bacillus sp. No. 170 (FERM BP-467) having the ability to produce and secrete penicillinase was cultured at 30° C. with shaking for 19 hours in a broth (containing 2.0 g of glycerol, 5.0 g of yeast extract, 5.0 g of polypeptone, 1.0 g of $K_2HPO_4$, 0.2 g of $MgSO_4.7H_2O$, 10 g of $NaHCO_3$ in one liter of deionized water; pH 9.0). The cells in the latter logarithmic phase were collected, and chromosomal DNA was extracted therefrom by the phenol extraction method and purified to obtain 5 mg of the chromosomal DNA.

The chromosomal DNA (10 micrograms) obtained was digested with the restriction enzyme Hind III at 37° C. for 5, 10, 20, 30 and 60 minutes to obtain DNA fragments.

Plasmid pMB9 (Bethesda Research Laboratories, U.S.A., tetracyclin resistant ($Tet^r$)) used as a vector was cleaved with Hind III, then heated at 65° C. for 5 minutes, and then mixed with the DNA fragments. The mixture was treated with $T^4$ phage DNA ligase at 10° C. for 24 hours and then heated at 65° C. for 5 minutes.

Two-fold volume of ethanol was added to the mixture. Plasmids carrying the chromosomal DNA fragments were precipitated and collected.

*Escherichia coli* HB101, which is a hybrid strain of *Escherichia coli* K-12 and *Escherichia coli* B, was inoculated in 10 ml of LB-broth (containing 10 g of tryptone (Difco Laboratories, Detroit, Mich.), 5 g of yeast extract, 1 g of glucose and 10 g of NaCl in one liter of deionized water; pH was adjusted to 7.0) and cultured at 37° C. with shaking until the latter logarithmic phase. The cells were collected and suspended under ice-cooled condition in a 0.03M $CaCl_2$ solution (final concentration) to obtain competent cells. The cell suspension and the plasmid solution were combined and kept under ice-cooled condition for 60 minutes. The mixture was heated at 42° C. for 1 to 2 minutes to introduce the plasmid DNA into the cells. This cell suspension was inoculated in fresh LB-broth and cultured at 37° C. for 3 to 5 hours with shaking. The cells were collected and washed to obtain transformants, from which *Escherichia coli* HB101 (pEAP2) (FERM BP-468) was isolated. The cells were treated as follows to obtain purified plasmid pEAP2.

Cell pellets
    10 ml, 20% Sucrose, 50 mM Tris, 1 mM EDTA pH8. Suspended, Keep on ice.
50 ml polypropylene centrifuge tube.
    2 ml, 0.25 M EDTA.
    1 ml, Lysozyme (5 mg/ml of 0.025 M Tris, pH8.)
    0.1 ml, R Nases (10 mg/ml)
↓
Cell lysis. Mix gently. Stand 15 to 30 min. on ice.
    5 ml, 3x Triton. Mix gently. Stand 15 to 45 min. on ice.
↓

-continued

Centrifugation. 17,000 rpm, 40 min. at 4° C.
↓
Supernatant soln. in plastic cylinder.
↓
250 ml glass bottle.
    ⅓ vol DD $H_2O$
    ⅓ vol Cold saturated phenol. Mix gently
↓
Centrifugation. 6,500 rpm, 15 min. at 4° C.
↓
Upper phase.
    Equal vol. of phenol; Chloroform.
↓
Centrifugation. 6,500 rpm, 15 min. at 4° C.
↓
Upper phase in 250 ml bottle.
    1/25 vol 5 M NaCl.
    2 vol EtOH at −20° C.
    Over night at −20° C.
↓
Centrifugation. 6,500 rpm, 60 min. at −20° C.
↓
DNA pellet. Dry excess liquid.
    5 ml A-50 buffer, resuspended.
    1 ml sterile 80% glycerol, mix gently.
↓
A-50 column. (2 × 35 cm, 1 fraction = 4 ml.)
↓
DNA fraction. ($A_{260}$ peak.)
    2 vol EtOH at −20° C. Over night at −20° C.
↓
Centrifugation. 6,500 rpm, 60 min. at −20° C.
↓
DNA pellet.
    2.1 ml TEN buffer in 5 ml cellulose nitrate tube.
    2.2 g CsCl, mix.
    (In dark.)
    150 μl PdI (2 mg/ml). Mix well.
    2 ml mineral oil on top of tube.
↓
CsCl gradient centrifugation. 36,000 rpm, 40 hr at 20° C.
    Upper band; chromosomal & nicked DNA.
    Visible with UV.
    Lower band; covalently closed p-DNA.
↓
Collect of lower band DNA by drop wise.
↓
Dowex 50W-X8 column. UV check.
    (In light.)
↓
Dialysis against 2 to 4 liters of 10 mM Tris, 1 mM EDTA PH8.
    Over night at 4° C.
↓

-continued

In 30 ml cortex centrifuge tube.
- 1/25 vol 5 M NaCl.
- 2 vol EtOH at −20° C.
- Over night at −20° C.

↓

Centrifugation. 6,500 rpm, 60 min. at −20° C.

↓

DNA precipitates.
- 1-2 ml TEN buffer.

↓

Purified plasmid DNA (1 mg/1-broth). Stored at −20 to 70° C.

EXAMPLE 2

Preparation of the xylanase DNA fragment

Aeromonas sp. No. 212 (ATCC 31085) having the ability to produce xylanase was cultured in a broth (containing 0.5% ammonium sulfate, 1.5% pulp flock, 0.02% glucose, 0.1% yeast extract, 0.02% $MgSO_4 \cdot 7H_2O$ and 0.2% $K_2HPO_4$ and adjusted to pH9 with a 7% $NaHCO_3$ solution in water) at 37° C. for 10 hours with shaking until the latter logarithmic phase. The cells were collected, and chromosomal DNA was extracted therefrom by the phenol extraction method and purified to obtain 3 mg of the chromosomal DNA.

The chromosomal DNA (10 micrograms) was digested with Hind III at 37° C. for 5, 10, 20, 30 and 60 minutes to obtain DNA fragments.

Plasmid pBR 322 (Bethesda Research Laboratories, U.S.A., tetracyclin resistant ($Tet^r$) and ampicillin resistant ($Amp^r$)) used as a vector was fully cleaved with Hind III, then heated at 65° C. for 5 minutes, and then mixed with the DNA fragments. The mixture was treated with $T_4$ ligase at 10° C. for 24 hours and then heated at 65° C. for 5 minutes. Two-fold volume of ethanol was added to the mixture. Plasmids carrying the chromosomal DNA fragments were precipitated and collected.

Escherichia coli HB101 was inoculated in 10 ml of LB broth (containing 10 g of tryptone (Difco Laboratories), 5 g of yeast extract, 20 μg/ml of ampicillin and 10 g of NaCl but not containing glucose; pH 7.0) and cultured at 37° C. with shaking until the latter logarithmic phase. The cells were collected and suspended under ice-cooled condition in a 0.03M $CaCl_2$ solution in water (final concentration) to obtain competent cells. The cell suspension and the plasmid solution were combined and kept under ice-cooled condition for 60 minutes. The mixture was heated at 42° C. for 1 to 2 minutes to introduce the plasmid DNA into the cells. The cell suspension was inoculated in a broth containing 100 μg/ml of ampicillin and 0.5% of xylan and cultured. Four strains having xylanase activity were isolated from among 3,000 strains. The four strains were cultured in LB broth, from which plasmids were isolated and purified in the same manner as in Example 1. The analysis of the sequence structure of the plasmids showed that the same DNA fragment had been inserted in the same direction. It was confirmed by Southern's method that the DNA fragment was one derived from Aeromonas sp. No. 212.

EXAMPLE 3

Construction of pXP102-3

The plasmid pAX1 (5 micrograms) carrying the xylanase DNA fragment was cleaved with the restriction enzyme Bgl II (15 units) at 37° C. for 60 minutes to obtain DNA fragments.

The plasmid pEAP2 (5 micrograms) carrying the penicillinase DNA fragment was fully cleaved with Hind III at 37° C. for 60 minutes, then treated at 65° C. for 5 minutes and then mixed with the DNA fragments obtained from the plasmid pAX1. The mixture was treated with $T_4$ phage DNA ligase and then heated at 65° C. for 5 minutes.

To the mixture, there were added Bam HI (15 units) and Bgl II (15 units) and then the mixture was treated at 37° C. for 60 minutes to selectively cleave pEAP2 and pAX1and subsequently treated with $T_4$ phage DNA ligase so that the plasmid pXP102-3 was concentrated.

Escherichia coli HB101 was inoculated in LB broth not containing glucose and cultured at 37° C. with shaking until the latter logarithmic phase. The cells were collected and suspended under ice-cooled condition in $CaCl_2$ solutions in water (concentration of final one was 0.03M) to obtain competent cells. The cell suspension and the plasmid solution were combined and kept under ice-cooled condition for 60 minutes. The mixture was then heated at 42° C. for 1 to 2 minutes to introduce the plasmid into the cells. The cell suspension was inoculated in LB broth not containing glucose and cultured. A strain having ampicillin resistance (20 gamma) and xylanase activity was isolated. The transformant Escherichia coli HB101 (pXP102-3) (FERM BP-951) was obtained, which was then treated in the same manner as in Example 1 to obtain the plasmid pXP102-3.

EXAMPLE 4

Escherichia coli HB101 (pAX1) (FERM BP-950) and Escherichia coli HB101 (pXP102-3) (FERM BP-951) obtained in Examples 2 and 3, respectively were cultured at 37° C. with shaking in LB broth not containing glucose (containing 10 g of tryptone (Difco), 5 g of yeast extract, 20 μg/ml of ampicillin and 10 g of NaCl in one liter of water and adjusted to pH 7.0). The cell growth (cell weight) was measured by optical density at 660 nm. Penicillinase activity was measured by a modified Sargent's method (Sawai et al: Antimicrob. Agents Chemother. 13, 910 (1978)), wherein the amount of penicillinase hydrolysing one micromole of benzyl penicillin per minute at 30° C. was taken as one unit. Xylanase activity was measured as follows: To 0.05 ml of enzyme solution, there were added 0.1 ml of xylan solution (produced by SEI-KAGAKU KOGYO, Japan) and 0.1 ml of 0.2M Tris malate buffer (pH 8.0) and the reaction was allowed to proceed at 40° C. for 10 minutes. DNS (3.5-dinitrosalicylic acid) (1 ml) was added and reacted at 100° C. for 5 minutes. Water (4 ml) was added and absorbance at 510 nm was measured. The amount of enzyme showing a reducing power producing 1 mg of xylose per minute was taken as one unit of xylanase.

Beta-galactosidase activity was measured as follows: 100 microliters of enzyme solution and 900 microliters of Z buffer (containing 4.3 g of $NaHPO_4 \cdot 12H_2O$, 1.25 g of $NaH_2PO_4$, 0.15 g of KCl and 0.04 g of $MgSO_4$ in 200 ml of distilled water) were reacted at 30° C. for 5 minutes. Arthonitropyranosyl galactoside (0.2 ml) (4 mg/ml in 0.1M phosphate buffer (pH 7)) was added and reacted at 30° C. for 10 minutes. A 2% Na$_2$CO$_3$ solution in water (1.8 ml) was added and absorbance at 420 nm was measured. The enzyme activity was expressed as the increase in the absorbance per ml of enzyme solution per minute.

Beta-lactamase activity was measured by the same method as that for penicillinase.

Figure 4:
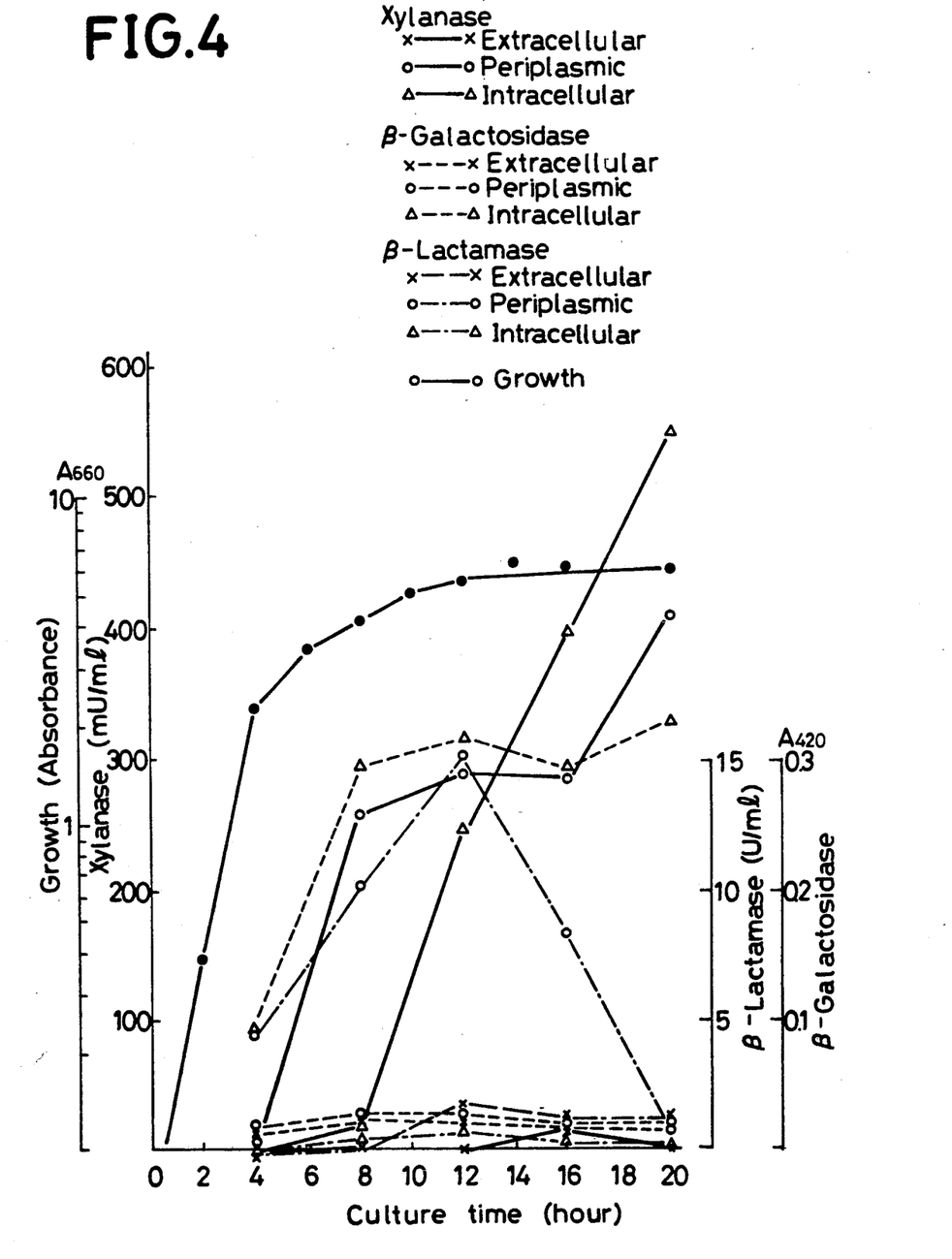
FIG. 4 shows bacterial growth and production of xylanase, beta-galactosidase and beta-lactamase by *Escherichia coli* HB101 (pAX1).

FIG. 4 shows the growth and production of xylanase, beta-galactosidase and beta-lactamase by *Escherichia coli* HB101 (pAX1). Xylanase was accumulated mainly inside the cell and in the periplasmic space but slightly outside the cell. Beta-galactosidase was accumulated mainly inside the cell but slightly in the periplasmic space and outside the cell. Betalactamase was accumulated first in the periplasmic space but it was not found therein after 20 hours.

Figure 5:
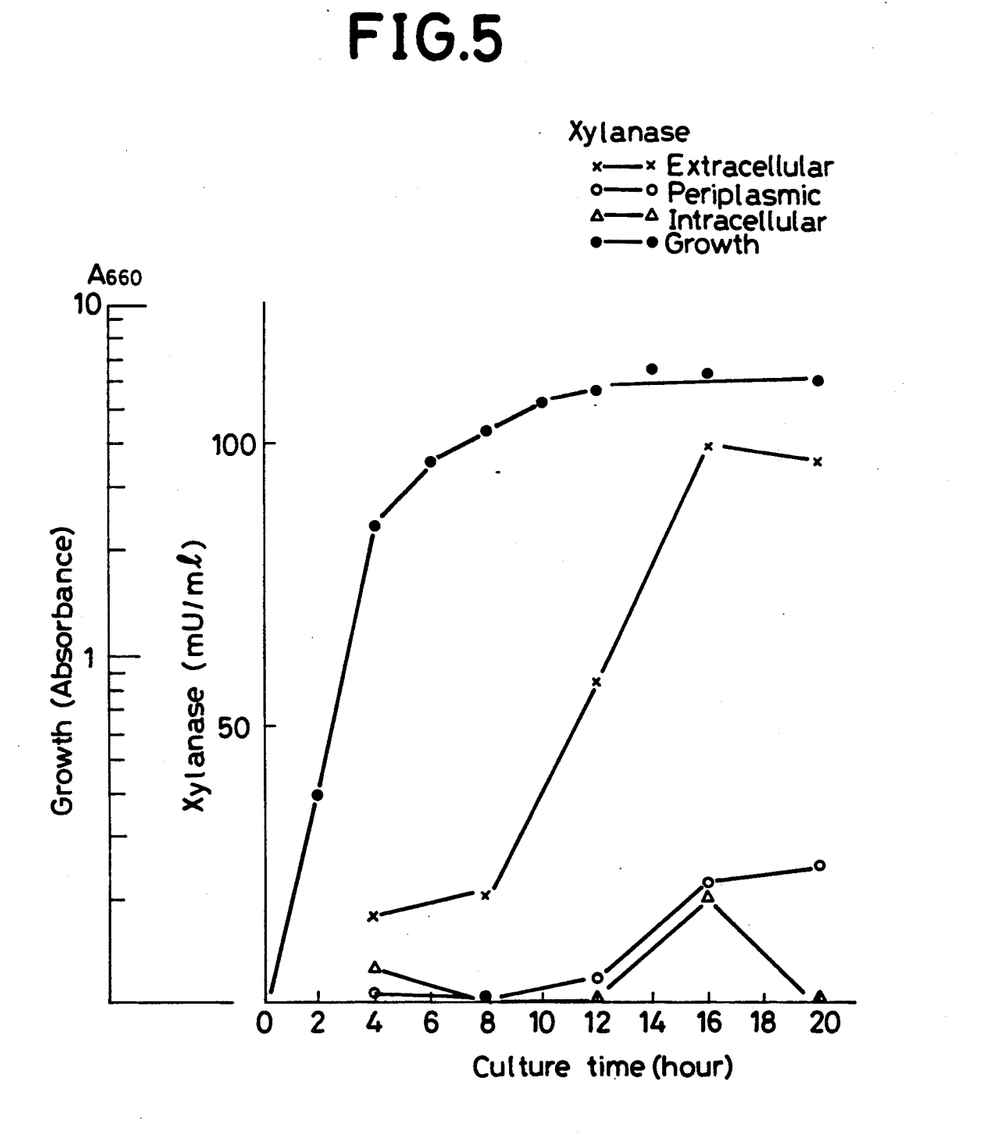
FIG. 5 shows bacterial growth and production of xylanase by *Escherichia coli* HB101 (pXP102-3) of this invention.

FIG. 5 shows production of xylanase by *Escherichia coli* HB101 (pXP102-3). Almost all xylanase produced was secreted outside the cell in 16 to 20 hours. Xylanase was found in a small amount in the periplasmic space but not inside the cell.

The transformant, *Escherichia coli* HB101 (pXP102-3), containing the plasmid pXP102-3 which was constructed by inserting the xylanase DNA fragment obtained from *Escherichia coli* HB101 (pAX1) which produces xylanase but does not secrete it into media, into the plasmid pEAP2 of *Escherichia coli* HB101 (pEAP2) which produces penicillinase and secretes it into media, produces and secretes into media not only penicillinase but also xylanase.

Figure 6:
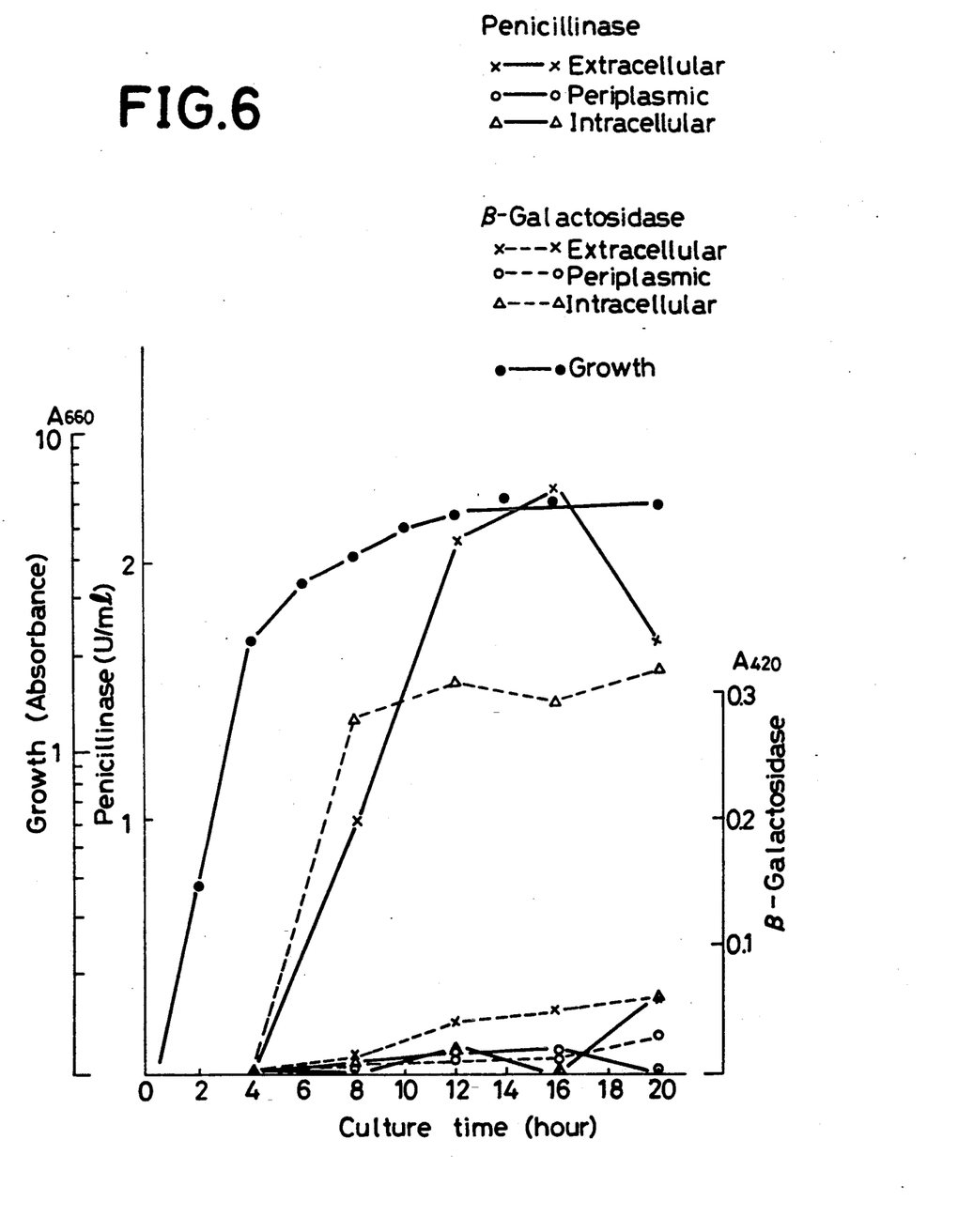
FIG. 6 shows bacterial growth and production of penicillinase and beta-galactosidase by *Escherichia coli* HB101 (pXP102-3) of this invention.

FIG. 6 shows production of penicillinase and beta-galactosidase by *Escherichia coli* HB101 (pXP102-3). Almost all penicillinase produced was secreted and accumulated outside the cell. In contrast, almost all beta-galactosidase was accumulated inside the cell and was not secreted outside the cell.

What we claim is:

1. A plasmid which is capable of transforming a host cell from a strain of the genus Escherichia into a cell capable of expressing and secreting heterologous penicillinase and xylanase, said plasmid consisting essentially of:
    a) a first chromosomal DNA fragment from the genus Bacillus coding for penicillinase; and
    b) a second DNA fragment, operably linked for autonomous expression in a transformed host to said first DNA fragment, and expressing said xylanase, said second DNA fragment consisting of a chromosomal DNA fragment from a strain of the genus Aeromonas coding for xylanase.

2. The plasmid of claim 1, wherein said plasmid is the plasmid pXP102-3 (FERM BP-951).

3. The plasmid of claim 1, wherein said strain of the genus Bacillus is Bacillus No. 170 (FERM BP-467).

4. The plasmid of claim 1, wherein said strain of the genus Aeromonas is Aeromonas sp No. 212 (ATCC 31085).

5. A transformed strain of the genus Escherichia being capable of expressing and secreting heterologous penicillinase and xylanase, which strain comprises a plasmid consisting essentially of:
    a) a first chromosomal DNA fragment from the genus Bacillus coding for penicillinase; and
    b) a second DNA fragment, operably linked for autonomous expression to said first DNA fragment, and for expressing said xylanase, said second DNA fragment consisting of a chromosomal DNA fragment from a strain of the genus Aeromonas coding for xylanase.

6. The transformed strain of claim 5, wherein said plasmid is the plasmid pXP102-3 (FERM BP-951).

7. The transformed strain of claim 5, wherein said strain of the genus Bacillus is Bacillus No. 170 (FERM BP-467).

8. The transformed strain of claim 5, wherein said strain of the genus Aeromonas is Aeromonas sp. No. 212 (ATCC 31085).

9. A method for producing penicillinase and xylanase, which comprises cultivating a transformed strain of the genus Escherichia in a suitable nutrient broth, thereby accumulating said penicillinase and xylanase, and separating the thus-produced penicillinase and xylanase from the broth, wherein said transformed strain is capable of expressing and secreting heterologous penicillinase and xylanase, and which strain comprises a plasmid consisting of:
    a) a first chromosomal DNA fragment from the genus Bacillus coding for penicillinase; and
    b) a second DNA fragment, operably linked for autonomous expression to said first DNA fragment, and for expressing said xylanase, said second DNA fragment consisting of a chromosomal DNA fragment from a strain of the genus Aeromonas coding for xylanase.

10. The method of claim 9, wherein the suitable nutrient broth contains an inorganic salt selected from the group consisting of sodium salts and potassium salts, and a carbon source selected from the group consisting of bran and xylan.

11. The method of claim 10, wherein the inorganic salt is used in an amount of 0.1 to 3.0% by weight on the basis of the weight of the medium.

12. The method of claim 9, wherein the transformed strain is cultured for 12 to 48 hours.

* * * * *